United States Patent [19]

Locicero

[11] Patent Number: 4,834,967
[45] Date of Patent: May 30, 1989

[54] METHOD OF REMOVING TICKS AND LEECHES FROM MAMMALS

[76] Inventor: Frank Locicero, 10 Ellen Ct., Wayside, N.J. 07712

[21] Appl. No.: 169,442

[22] Filed: Mar. 17, 1988

[51] Int. Cl.$^4$ .............................................. A01N 25/00
[52] U.S. Cl. ..................................... 424/45; 424/405; 424/409; 424/443
[58] Field of Search ........................... 424/45; 222/538

[56] References Cited

U.S. PATENT DOCUMENTS

| | | | |
|---|---|---|---|
| 2,833,669 | 5/1958 | Ziegler | 424/443 |
| 3,161,622 | 12/1964 | Harrington et al. | 424/443 |
| 3,303,091 | 2/1987 | Mallander et al. | 424/45 |
| 4,096,974 | 6/1978 | Haber | 222/538 |
| 4,112,065 | 9/1978 | Enders | 424/45 |
| 4,160,336 | 7/1979 | Query et al. | 43/132.1 |
| 4,174,295 | 11/1979 | Bargigia | 424/45 |
| 4,413,756 | 11/1983 | Kirley | 222/538 |

FOREIGN PATENT DOCUMENTS

| | | | |
|---|---|---|---|
| 0003367 | of 1870 | United Kingdom | 424/443 |
| 0001459 | of 1878 | United Kingdom | 424/443 |

OTHER PUBLICATIONS

Charles J. McDonald, Cytotoxic Agents for Use in Dermatology, CME article, vol. 12, No. 5, Part 1, May 1, 1985.

*Primary Examiner*—Thurman K. Page
*Assistant Examiner*—P. Prater
*Attorney, Agent, or Firm*—Wegner & Bretschneider

[57] ABSTRACT

A method for the removal of ticks and leeches from the skin of mammals including man, dogs, cats, sheep and cattle, wherein the tick or leech is directly sprayed with a compressible liquid refrigerant, in aerosol form, in an amount sufficient to freeze, ill and dislodge the tick or leech from the skin.

12 Claims, No Drawings

METHOD OF REMOVING TICKS AND LEECHES FROM MAMMALS

The present invention is directed to a method for the removal of ticks and leeches from mammals. Ticks are members of the superfamily Ixodoidea, of wingless, blood sucking arachnids; or, for the purposes of this application, the term "tick" also includes any degenerative two winged parasitic insect. These arachnids are usually parasitic on mammals including man, dogs, cats, cattle, sheep or any other warm blooded animal of the class Mammalia. A leech is defined as any of a number of annelid worms of the class Hirudinea, having well-developed suckers at each end. Leeches are also parasitic on mammals.

The conventional processes for tick removal present various problems. These processes include the use of flea and tick pet collars, flea and tick shampoos and soaps, suffocation and heat.

Flea and tick pet collars require continuous exposure of the animal to the chemicals administered by the collar. Such exposure may have a deleterious effect on the animal's health. Further, many such collars are not adequately effective against ticks.

Flea and tick shampoos and soaps also require relatively long exposure to harsh chemicals. Use of these products on aminals involves a messy, time consuming process which includes wetting the animal with water, applying the soap or shampoo, working the soap or shampoo into a lather and allowing it to remain in contact with the skin for an adequate amount of time, and finally thoroughly rinsing the soap or shampoo from the animal. Failure to thoroughly rinse the soap or shampoo or prolonged exposure of the skin to the soap or shampoo can cause various skin problems. Failure to allow the soap or shampoo to remain in contact with the skin for an adequate amount of time may result in the tick(s) remaining attached to the skin.

Ticks have been removed from humans by coating the tick with grease, vaseline or nail polish to bring about suffocation of the tick. Also, ticks have been removed by touching the head of the tick with a hot match. The above methods are messy, time consuming and dangerous in the latter case. Further, the mouth parts of the tick may remain in the skin and become sites of infection.

Traditionally, leeches have been removed by pulling them from the skin. This method may be painful and often leaves an unsightly puckered mark on the skin.

It has been discovered that compressible liquid refrigerants, applied directly on a tick or leech, effect the freezing, death and dislodgment of the tick or leech. The method of the present invention allows the quick, painless and efficient removal of ticks and leeches from an area of skin of a mammal without any deleterious effect on the mammal's health.

The object of the present invention is to provide a method for the removal of ticks and leeches from the skin of mammals.

The object of the present invention is fulfilled by providing a method for removal of ticks and leeches from an area of skin of a mammal wherein a liquid refrigerant is applied to the tick or leech so as to freeze, kill and dislodge the tick or leech from the skin.

The object of the present invention is further fulfilled by providing a method for removal of ticks and leeches from an area of skin of a mammal wherein a compressible liquid refrigerant in aerosol form, is sprayed directly on the tick or leech so as to freeze and kill the tick or leech and allow it to be dislodged from the skin.

The present method is defined by the application of a liquid refrigerant to a tick or leech, in an amount sufficient to effect dislodgment of the tick or leech. A refrigerant is defined as a liquid that cools or freezes something by vaporization at a low temperature. The liquid refrigerants include Freon R-12, Freon R-22, Freon R-502, liquid nitrogen and carbon dioxide.

More specifically, the refrigerant is in aerosol (gas under pressure is used to aerate the liquid refrigerant in a small container and dispense it through a valve in the form of a spray) form and can be sprayed directly on a tick via a capillary-like extension tube attached to the nozzle of an aerosol container of liquid refrigerant. This container can have a metered spray output. Liquid refrigerants in aerosol form having a metered spray output include those marketed by Phillips ECG Inc. These containers, manufactured by American Can Co., are equipped with a variable control valve, manufactured by Precision Valve Co., which allows a low, medium or high spray. Each discharge of the container with the valve set on low, medium or high is approximately 1 second in duration with the amount of refrigerant released varying.

Removal of the tick or leech is accomplished by placing the free end of the capillary-like extension tube attached to the nozzle of the container of liquid refrigerant, directly against the tick or leech. The container is discharged as necessary to dislodge the tick or leech. Upon completion of spraying, the tick or leech is frozen, dead and dislodged. During discharge only the tick or leech is sprayed, so little or no overspray to the skin of the mammal is needed. Since the refrigerant does not contact the skin, there is no significant lowering of skin temperature. Final removal of the tick or leech is accomplished by picking the frozen, dead tick or leech from the skin with tweezers.

The following examples further illustrate the present invention in detail, but are not to be construed to limit the scope thereof.

EXAMPLE 1

A tick of approximately ⅛ inch in diameter is removed from the skin of a dog by:

1. spreading the dog's fur to reveal the tick;
2. placing the free end of a capillary-like extension tube attached to the nozzle of a container, manufactured by American Can Co., of Freon R-12, manufactured by DuPont Chemicals, a halogenated hydrocarbon aerosol refrigerant having a metered spray output, directly against the tick;
3. setting the variable control valve, manufactured by Precision Valve Co., of the container on "low";
4. discharging the container once, in approximately 1 second, approximately 1.3 grams or 1 milliliter of Freon R-12 is released;
5. upon discharge the tick is frozen, dead and dislodged;
6. removing the frozen, dead tick by picking it from the skin with a pair of tweezers;
7. the skin temperature of the dog is not lowered;
8. no signs of pain or discomfort to the dog are observed.

EXAMPLE 2

A tick of approximately ¼ inch in diameter is removed from the skin of a dog by:
1. spreading the dog's fur to reveal the tick;
2. placing the free end of a capillary-like extension tube attached to the nozzle of a container, manufactured by Americal Can Co., of Freon R-12, manufactured by DuPont Chemicals, a halogenated hydrocarbon aerosol refrigerant, having a metered spray output, directly against the tick;
3. setting the variable control valve, manufactured by Precision Valve Co., of the container on "low";
4. discharging the container twice, releasing a total of approximately 2.6 grams or 2 milliliters of Freon R-12 in approximately 2 seconds;
5. upon the second discharge the tick is frozen, dead and dislodged;
6. removing the frozen, dead tick by picking it from the skin with a pair of tweezers;
7. the skin temperature of the dog is not lowered;
8. no signs of pain or discomfort to the dog are observed.

EXAMPLE 3

A tick of approximately 1/6 inch in diameter is removed from a human patient by:
1. placing a cotton swab saturated with liquid $N_2$ directly against the tick;
2. upon application the tick is frozen, dead and dislodged;
3. removing the frozen, dead tick by picking it from the skin with a pair of tweezers;
4. the skin temperature of the patient is not lowered;
5. no ill effects to the patient are observed.

EXAMPLE 4

A leech of approximately 2 inches in length is removed from a human patient by:
1. placing the free end of a capillary-like extension tube attached to the nozzle of a container manufactured by American Can Co., of Freon R-12, manufactured by DuPont Chemicals, a halogenated hydrocarbon refrigerant, having a metered spray output, directly against the end of the leech attached to the skin;
2. setting the variable control valve, manufactured by Precision Valve Co., of the container on "low";
3. discharging the container four times, releasing a total of approximately 5.2 grams of 4 milliliters of Freon R-12 in approximately 4 seconds;
4. upon the fourth discharge, the leech is frozen, dead and dislodged;
5. removing the frozen, dead leech, by picking it from the skin with a pair of tweezers;
6. the skin temperature of the patient was not lowered;
7. no ill effects to the patient are observed.

I claim:

1. A method for the removal of ticks and leeches from an area of skin of a mammal comprising:
   directly applying to the tick or leech a fluid consisting essentially of a compressible liquid refrigerant in such a manner that there is no significant lowering of skin temperature and in an amount and duration sufficient to freeze the tick or leech to thereby effect dislodgment of the tick or leech from the skin.

2. A method according to claim 1, wherein said compressible liquid refrigerant is in aerosol form and is sprayed on the affected area.

3. A method according to claim 2, wherein said refrigerant is directly sprayed through a small bore extension tube, with one end of the tube attached to the nozzle of an aerosol container of the refrigerant and with the other end of the tube held directly against the tick or leech, such that upon discharge of the can substantially only the tick or leech is sprayed.

4. A method according to claim 1, wherein said refrigerant is directly applied to said tick or leech by placing a cotton swab saturated with said refrigerant directly against the tick or leech.

5. A method according to claim 4, wherein said refrigerant comprises liquid nitrogen.

6. A method according to claim 3, wherein said refrigerant comprises carbon dioxide.

7. A method according to claim 3, wherein said refrigerant comprises dichlorodifluoromethane.

8. A method according to claim 3, wherein said refrigerant comprises dichlorofluoromethane.

9. A method according to claim 3, wherein said refrigerant comprises a mixture comprising 48.8 percent by weight chlorodifluoromethane and 51.2 percent by weight chloropentafluoroethane.

10. A method according to claim 3, wherein said tick is less than or equal to ¼ inch in diameter and is frozen, killed and dislodged by a single discharge of said aerosol container for approximately a 1 second duration whereby approximately 1 milliliter of refrigerant is released.

11. A method according to claim 3, wherein said tick is greater than or equal to ¼ inch in diameter and is frozen, killed and dislodged by discharging said aerosol container twice, with each discharge being approximately 1 second in duration and the total amount of refrigerant released is approximately 2 milliliters.

12. A method as in claim 1, wherein said refrigerant has a boiling point in the range of −320.4° F. to −21.62° F.

* * * * *

UNITED STATES PATENT AND TRADEMARK OFFICE
CERTIFICATE OF CORRECTION

PATENT NO. : 4,834,967

DATED : May 30, 1989

INVENTOR(S) : Frank LOCICERO

It is certified that error appears in the above-identified patent and that said Letters Patent is hereby corrected as shown below:

Claim 8, line 2, change "dichlorofluoromethane" to --chlorodiflouromethane--.

Signed and Sealed this

Twentieth Day of March, 1990

Attest:

JEFFREY M. SAMUELS

Attesting Officer

Acting Commissioner of Patents and Trademarks